United States Patent [19]

Offermanns et al.

[11] 4,055,653
[45] Oct. 25, 1977

[54] SULFUR CONTAINING TRIALKOXYBENZOYLAMINO CARBOXYLIC ACIDS

[75] Inventors: Heribert Offermanns, Grossauheim; Klaus Posselt, Wachtberg-Villiprott, both of Germany

[73] Assignee: Deutsche Gold- und Silber-Scheideanstalt vormals Roessler, Frankfurt, Germany

[21] Appl. No.: 687,504

[22] Filed: May 18, 1976

Related U.S. Application Data

[63] Continuation-in-part of Ser. No. 468,087, May 8, 1974, Pat. No. 3,981,910.

[30] Foreign Application Priority Data

May 15, 1973 Austria .................................. 4232/73

[51] Int. Cl.² .................... A61K 31/24; A61K 31/38; A61K 31/195
[52] U.S. Cl. .................................. 424/275; 424/309; 424/319
[58] Field of Search ................ 424/275, 330, 309, 319

[56] References Cited
FOREIGN PATENT DOCUMENTS

| | | |
|---|---|---|
| 2,129,877 | 3/1972 | France |
| 2,131,680 | 1/1972 | Germany |
| 2,131,675 | 6/1971 | Germany |

*Primary Examiner*—Stanley J. Friedman
*Attorney, Agent, or Firm*—Cushman, Darby & Cushman

[57] ABSTRACT

Compounds are prepared of the formula:

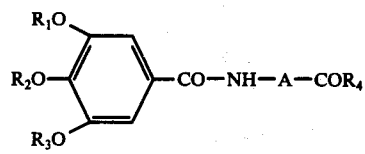

I wherein A is a straight or branched chain alkylene or alkylidene radical having 2 to 5 carbon atoms and which is substituted by an alkylthio group having 1 to 4 carbon atoms, a carboxymethyl thio group, a carboxyethyl thio group, an alkylsulfonyl group having 1 to 4 carbon atoms, a mercapto group, or the substituent on A together with $-COR_4$ forms a 4 to 7 membered thiolactone ring, or A is substituted by an acylmercapto group wherein the acyl is benzoyl, a benzoyl radical substituted with one, two or three alkoxy groups with 1 to 6 carbon atoms, an alkanoyl radical of 1 to 6 carbon atoms, an alkenoyl radical of 3 to 6 carbon atoms, $R_1$, $R_2$ and $R_3$ are the same or different and are alkyl groups of 1 to 5 carbon atoms and one of $R_1$, $R_2$ and $R_3$ also can be hydrogen or the acyl radical of an alkanoic acid of 2 to 4 carbon atoms and $R_4$ is a hydroxy group or an alkoxy group with 1 to 5 carbon atoms and their pharmacologically acceptable salts. The compounds are pharmacodynamically active and are suited for prophylaxis and treatment of heart illnesses such as cardiac ischemia, cardiac infarct, heart rhythm and circulatory disturbances.

46 Claims, No Drawings

SULFUR CONTAINING TRIALKOXYBENZOYLAMINO CARBOXYLIC ACIDS

This application is a continuation-in-part of application Ser. No. 468,087, filed May 8, 1974. Now U.S. Pat. 3,981,910.

The invention is directed to compounds of the formula:

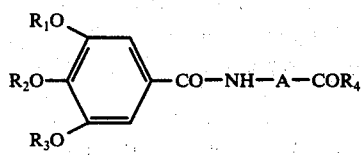

wherein:

A is a straight or branched chain alkylene or alkylidene radical having 2 to 5 carbon atoms and which is substituted by an alkylthio group having 1 to 4 carbon atoms, a carboxymethyl thio group, a carboxyethyl thio group, an alkylsulfonyl group having 1 to 4 carbon atoms, a mercapto group, or the substituent on A together with —$COR_4$ forms a 4 to 7 membered thiolactone ring, or A is substituted by an acylmercapto group wherein the acyl is benzoyl, a benzoyl radical substituted with one, two or three alkoxy groups with 1 to 6 carbon atoms, an alkanoyl radical of 1 to 6 carbon atoms, an alkenoyl radical of 3 to 6 carbon atoms;

$R_1$, $R_2$ and $R_3$ are the same or different and are alkyl groups of 1 to 5 carbon atoms and one of $R_1$, $R_2$ and $R_3$ also can be hydrogen or the acyl radical of an alkanoic acid of 2 to 4 carbon atoms, and $R_4$ is a hydroxy group or an alkoxy group with 1 to 5 carbon atoms and their pharmacologically acceptable salts. The compounds are pharmacodynamically active and are suited for prophylaxis and treatment of heart illnesses such as cardiac ischemia, cardiac infarct, heart rhythm and circulatory disturbances.

As alkylidene groups is meant a divalent alkyl group in which two single bonds (both bonds of A) go from a single carbon atom, i.e., for example, an $<CH_2$ group in which one or both hydrogen atoms are replaced by a straight or branched alkyl radical with 1 to 5 carbon atoms. Examples of these types of alkylidene groups are: $CH_3$ . CH$<$, $CH_3$—$CH_2$ . CH$<$, $CH_3$ . $(CH_2)2$ . CH$<$, $CH_3$ . $(CH_2)3$ . CH$<$, $CH_3$ . $(CH_2)4$ . CH$<$, $CH_3$ . CH($CH_3$) . $CH_2$—CH $<$, $CH_3$ . $CH_2$ . CH($CH_3$) . CH$<$, $CH_3$—$CH_2$—C($CH_3$)$<$, $(CH_3)2C<$, $(C_2H_5)2C<$, $C_3H_7$-C($CH_3$)$<$, $C_3H_7$-C($C_2H_5$)$<$.

Preferably A is a propylidene-1 group or a butylidene-1 group which is substituted in the 3 or 4 position by an alkylsulfonyl group, mercapto group or one of the above mentioned alkylated or acylated mercapto groups.

The alkyl group or alkoxy group as such or as part of another group (for example in the alkylmercapto group or alkylsulfonyl group) generally consists of 1 to 3 carbon atoms. $R_1$ is preferably methyl. In case one of the radicals $R_1$, $R_2$ and $R_3$ is hydrogen or an acyl radical then it is preferably $R_2$.

The acyl radical for example is derived from a saturated aliphatic carboxylic acid with 2 or 3 carbon atoms.

In addition to the specific compounds set forth in the working examples, other representative compounds within the invention include:

D,L-N-(3,4,5-triethoxy-benzoyl)-methionine;
D-N-(3,4,5-tripropoxy-benzoyl)-methionine;
L-N-(3,4,5-tributoxy-benzoyl)-methionine;
D,L,N-(3,4,5-triamyloxy-benzoyl)-methionine;
D,L-N-(3,5-dimethoxy-4-ethoxy-benzoyl)-methionine;
D,L-N-(3,5-dimethoxy-4-hydroxy-benzoyl)-methionine;
D,L-N-(3,5-dimethoxy-4-acetoxy-benzoyl)-methionine;
D,L-N-(3,5-dimethoxy-4-propionyloxy-benzoyl)-methionine;
D,L-N-(3,5-dimethoxy-4-butyryloxy-benzoyl)-methionine;
D,L-N-(3,5-diethoxy-4-hydroxy-benzoyl)-methionine;
D,L-N-(3,4,5-triethoxy-benzoyl)-ethionine-sulfone;
D,L-N-(3,4,5-tripropoxy-benzoyl)-homocysteinethiolactone;
D,L-N-0-(3,4,5-trimethoxy-benzoyl)-methionine methyl ester;
D,N-(3,4,5-trimethoxy-benzoyl)-methionine ethyl ester;
L-N-(3,4,5-trimethoxy-benzoyl)-methionine propyl ester;
D,L-N-(3,4,5-trimethoxy-benzoyl)-methionine butyl ester;
D,L-N-(3,4,5-trimethoxy-benzoyl)-methionine isobutyl ester;
D-N-(3,4,5-trimethoxy-benzoyl)-methionine sec. butyl ester;
D,L-N-(3,4,5-trimethoxy-benzoyl)-methionine amyl ester;
D,L-N-(3,4,5-trimethoxy-benzoyl)-methionine-sulfone methyl ester;
D,L-N-(1-carboxy-3-propylthiopropyl)-3,4,5-trimethoxy benzamide;
D,L-N-(1-carboxy-3-butylthiopropyl)-3,4,5-trimethoxy benzamide;
N-(1-carboxyl-2methylthioethyl)-3,4,5-trimethoxy benzamide, having the formula:

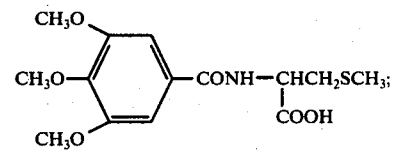

N-(1-carboxyl-2-ethylthioethyl)-3,4,5-trimethoxybenzamide;
N-(1-carboxyl-2-methylsulfonyethyl)-3,4,5-trimethoxybenzamide;
N-(1-carboxyl-4-methylthiobutyl)-3,4,5-trimethoxybenzamide;
N-(1-carboxyl-5-ethylthioamyl)-3,4,5-trimethoxybenzamide;
N-(1carboethoxy-2-methylthioethyl)-3,4,5-trimethoxybenzamide;
N-(1-carboxy-2-methylthioethylidene)-3,4,5-trimethoxybenzamide;
N-(1-carboxy-2-methylsulfonylisopropylidene)-3,4,5-trimethoxybenzamide;
N-(1-carboxy-3-methylthiopropylidene)-3,4,5-trimethoxybenzamide;

N-(1carboxy-3-ethylthiopropylidene)-3,4,5-trimethoxybenzamide;
N-(1-carboxy-3-ethylsulfonylpropylidene)-3,4,5-trimethoxybenzamide
N-(1carboxy-4-methylthiobutylidene)-3,4,5-trimethoxybenzamide;
N-(1-carboxy-4-methylsulfonylbutylidene)-3,4,5-trimethoxybenzamide;
N-(1-carboxy-4-mercaptobutylidene)-3,4,5-trimethoxybenzamide;
N-(1-carboxy-3-acetylthiopropylidene)-3,4,5-trimethoxybenzamide;
N-(1-carboxy-5-methylthiopentylidene)-3,4,5-trimethoxybenzamide;
N-(1-carboxy-1-ethyl-3-methylthiopropylidene)-3,4,5-trimethoxybenzamide;
D,L-N-(3,4,5-trimethoxy-benzoyl)-cysteinethiolactone;
N-(1-carboxy-3-carboxymethylmercaptopropyl)-3,4,5-trimethoxybenzamide;
N-(1-carboxy-4-carboxyethylmercaptobutyl)-3,4,5-trimethoxybenzamide;
N-(1-carboxy-2-carboxymethylmercaptoethyl)-3,4,5-triethoxybenzamide;
D,L-N-(1-carboxy-3-propylsulfonylpropyl)-3,4,5-trimethoxybenzamide;
D,L-N-(1-carboxy-3-butylsulfonylpropyl)-3,4,5-trimethoxybenzamide;
D,L-N-(1-carboxy-3-mercaptopropyl)-3,4,5-trimethoxybenzamide;
D-N-(1-carboxy-4-mercaptobutyl)-3,4,5-trimethoxybenzamide;
L-N-(1-carboxy-2-mercaptoethyl)-3,4,5-trimethoxybenzamide;
D,L-N-(1-carboxy-3-benzoylthiopropyl)-3,4,5-trimethoxybenzamide;
D,L-N-(1-carboxy-3-(3', 4', 5'-trimethoxybenzoylthio)-propyl-3,4,5-trimethoxybenzamide;
D,L-N-(1-carboxy-4-p-methoxybenzoylthiobutyl)-3,4,5-trimethoxybenzamide;
D,L-N-(1carboxy-2-m,p-dimethoxybenzoylthioethyl)-3,4,5-trimethoxybenzamide;
D,L-N-(1-carboxy-3 (3', 4',5'-trihexoxybenzoylthiopropyl)-3,4,5-trimethoxybenzamide;
D,L-N-(1-carboxy-3-formylthiopropyl)-3,4,5-trimethoxbenzamide;
D,L-N-(1-carboxy-3-propionlthiopropyl)-3,4,5-trimethoxybenzamide;
D,L-N-(1-carboxy-2-acetylthioisopropylidene)-3,4,5-trimethoxybenzamide;
D,L-N-(1-carboxy-4-propionylthiobutylidene)-3,4,5-trimethoxybenzamide.

Any of the compounds of the invention can be made and used as the free base or in the form of a pharmaceutically acceptable salt, e.g., alkali metal and alkaline earth metal salts such as the sodium, potassium, magnesium, calcium, and barium salts, aluminum salts, zinc salts, iron salts, etc.

The compounds of the invention can take place using methods known in themselves including:

a. reacting a compound of the formula:

, $H_2N-A-COR_4$    II where A and $R_4$ are as defined above with a benzoic acid of the formula:

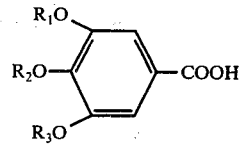

whose carboxyl group can also be activated, or b. treating a compound of formula I wherein A-$COR_4$ produces a lactone ring with an alkali mercaptide, e.g., sodium methyl mercaptide, and in a given case treating the compound obtained with an alkylating agent or hydrolyzing agent or splitting a thiolactone ring present.

Typical compounds within formula II are: methionine, ethionine, methionine, sulfone, ethionine sulfone homocrysteinethiolactone, cysteinethiolactone, methionine methyl ester, methionine ethyl ester, methionine propyl ester, methionine butyl ester, methionine isobutyl ester, methionine sec. butyl ester, methionine amyl ester, methonione sulfone methyl ester, methionine sulfone ethyl ester, 1-carboxy-3-propylthiopropylamine; 1-carboxy-3-butyl-thiopropylamine, 1-carboxy-2-methylthioethylamine; 1-carboxy-2-methylsulfonylethylamine; 1-carboxy-4-methylthiobutyamine;

1-carboxyl-5-methylthioamylamine; 1-carboethoxy-2-methylthioethylamine; 1-carboxy-2-methylthioethylamine, 1-carboxy-2-methylthioethyl amine; 1carboxy-1-methyl-2-methylsulfonylethylamine;

1-carboxy-3-ethylthiopropylamine; 1-carboxy-3-ethylsulfonyl-propylamine; 1-carboxy-4-methylthiobutyl amine;

1-carboxy-4-methylsulfonylbutyl amine;
1-carboxy-4-mercaptobutylamine;
1-carboxy-3-acetylthiopropylamine;
1-carboxy-5-methylthioamylamine;
1-carboxy-1-ethyl-3-methylthiopropylamine;
1-carboxy-3-carboxymethylmercaptopropylamine;
1-carboxy-4-carboxyethylmercaptobutyl amine;
1-carboxy-2-carboxymethylmercaptoethyl amine;
1-carboxy-3-propylsulfonylpropyl amine;
1-carboxy-3-butylsulfonylpropylamine;
1-carboxy-3-mercaptopropylamine;
1carboxy-4-mercaptobutylamine;
1-carboxy-2-mercaptoethylamine;
1-carboxy-3-benzoylthiopropylamine;
1-carboxy-3(3', 4', 5'-trimethoxybenzoylthiopropylamine);
1-carboxy-4-p-methoxybenzoylthiobutylamine;
1-carboxy-2-m,p-dimethoxybenzoylthio-ethylamine;
1-carboxy-3(3', 4', 5'-trihexoxybenzoylthiopropylamine);
1-carboxy-3-formylthiopropylamine;
1-carboxy-3-acetylthiopropylamine;
1-carboxy-3-propionylthiopropylamine;
1-carboxy-1-methyl-2-acetylthioisopropylamine;
1-carboxy-4-propionylthiobutylamine;

If benzoic acid derivatives of compounds of formula III are employed having activated carboxyl groups are employed in process (a) such compounds preferably have the formula:

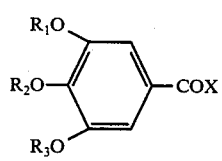

where X is halogen, the group —NωN, a group of the formula —OR', SR' or a group of the formula —O-SO$_3$H, —OPO (OH)$_2$, —OP (OR')$_2$, —O—As(OR')$_2$ or —OCO—R". R' is an alkyl group or in the case of —OR' or SR' for example can also be a phenyl radical, a p-nitrophenyl radical, a cyanomethyl radical or a carboxymethyl radical; R" can be straight or branched chain alkyl group, an alkoxy group, a phenoxy group, a carbobenzoyl group or the group:

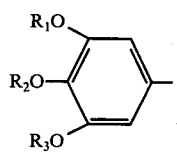

In case X is halogen, it is preferably chlorine or bromine, in case R' or R" is alkyl or alkoxy, then these are preferably of lower molecular weight and contain 1 to 6 carbon atoms.

The reaction of a compound of formula III or formula IV with a compound of formula II can take place in a conventional solvent or suspension agent such as water in a given case with addition of solvent facilitators, for example, lower aliphatic alcohols such as methyl alcohol, ethyl alcohol, propyl alcohol, isopropyl alcohol or butyl alcohol, lower aliphatic ketones, e.g., acetone and methyl ethyl ketone, or dimethyl formamide, or in indifferent media. Frequently, especially when X (in formula IV) is a halogen or the group —OCOR" it is appropriate to have present an acid binding material such as alkali hydroxides, e.g., sodium hydroxide and potassium hydroxide, alkali carbonates, e.g., sodium carbonate and potassium carbonate, alkali bicarbonates, e.g., sodium bicarbonate and potassium bicarbonate, alkali acetate, e.g., sodium acetate and potassium acetate, alkaline earth carbonates, e.g, magnesium carbonate, calcium carbonate and barium carbonate, trialkyl amines, e.g., triethylamine and tributylamine, pyridine and similar compounds or an excess of the compound of formula II. For this purpose the acid binding agent can also be used either alone or in admixture with other customary agents as solvents (for example, pyridine can be so used).

In case the free benzoic acid is used (compound of formula III) it is necessary to activate by the presence of a condensation agent such as dicyclohexyl carbodiimide, sulfurous acid bis alkylamides (for example SO[(CH$_3$)$_2$]$_2$), N,N'-carbonyldiimidazole, etc. (see *Organic Reactions, Vol.* 12 (1962) pages 205 and 239).

In case the starting material of formula II has a free carboxyl group, it is frequently appropriate to esterify this beforehand with benzyl alcohol or a lower aliphatic alcohol, having 1 to 6, especially 1 to 3 carbon atoms, such as any of the alcohols mentioned above, e.g., methyl alcohol, ethyl alcohol and isopropyl alcohol. This is especially true for the reaction with a free benzoic acid of formula III. This type of ester group can be split off from the end product with a base, for example, alcoholic alkali lye (for example, methanolic KOH or NaOH) or in a given case also by means of mineral acids such as hydrochloric acid or sulfuric acid in alcoholic or aqueous alcoholic solution at a temperature between 20° and 100° C.

In case in the compounds of formula II the portion A—COR$_4$ contains a carboxy group, this compound can also be added as an alkali salt (for example, the sodium salt or the potassium salt). This is especially true when the symbol X of the reaction component of formula IV is a halogen atom. In practice, the process is carried out in such amount that the free aminoacid is made into a paste with an about equal amount of water by weight and is then neutralized with about 30% soda lye. In a given case, excess soda lye is added as the acid acceptor. The mixture is cooled to −5° to +5° C., and then the trisubstituted benzoyl chloride gradually introduced with stirring while holding the temperature below 5° C. The molar proportions of aminoacid to benzoyl chloride range from about 1 to 1.5:1. The solution obtained is stirred for a long time (for example, 1 to 4 days). After the end of the addition the solution is decolorized with activated carbon and subsequently neutralized with dilute hydrochloric acid or sulfuric acid to a pH of 3. The precipitate which falls out is filtered off, washed with water and dried and finally recrystallized from water to ethanol.

The compounds of formula II can also be added as salts (for example the hydrochloride) or in the form of a derivative in which the amino group to be reacted is present in an activated form. One type of activation of the amino group, for example, can take place by conversion into the isocyanate radical (OCN-A-COR$_4$) by means of phosgene according to the method described by Goldschmidt in Liebigs Annalen der Chemie, Vol. 575 (1952), pages 217-226 (the entire disclosure of which is incorporated by reference), or by conversion into a dialkyl phosphoric acid amide ((Alkyl—0)$_2$P—N—A—COR$_4$) alkyl, for example, lower alkyl groups such as methol, ethyl, propyl, isopropyl or butyl, according to the method described by Anderson in the J. Amer. Chem. Soc. Vol. 73 (1951), page 501 et seq.; Anderson in J. Amer. Chem. Soc. Vol. 74 (1952), pages 5304-5306; pages 5307-5309 and 5309-5312 (the entire disclosure of all the Anderson articles is hereby incorporated by reference). Likewise it is possible to add the corresponding phosphorus azo compound in place of the amine of formula II. The phosphorus azo compound can be obtained by action of 2 mols of the compound II or PCl$_3$ (see Goldschmidt, Angewandte Chemie, Vol. 67 (1955), pages 471-475, the entire disclosure of which is hereby incorporated by reference).

In general the process of the invention is carried out at temperatures between −10° and +150° C. Independent of process conditions given above, there can be employed all of the methods and process conditions customarily employed in amide and peptide synthesis (see for example Houben-Weyl "Methoden der organischen Chemie", Vol. 8 (1952), pages 655-661 and "Organic Reactions" vol. 12 (1962), pages 157 et seq. (the entire disclosure of the cited pages from Houben-Weyl and Organic Reactions is hereby incorporated by reference).

In case the reaction component of formula III contains a hydroxy group (one of the radicals R$_1$ through R$_3$ is H), it is suitable to protect this beforehand by the customary acyl or other easily splittable protective groups used for this purpose. As this type of protective group there can be used, for example,e lower, in a given case, halogen substituted aliphatic (e.g., alkyl) acyl radicals such as formyl, tert. butylcarboxy, acetyl, propionyl, or trifluoroacetyl, the benzyl group, benzyl groups substituted in the benzene nucleus by halogen or nitro groups, for example, the p-bromobenzyl and the p-nitrobenzyl group, the α-phenylethyl group, the carbobenzoxy group, the carbonbenzthio group, the phthalyl radical, the trityl radical, the p-toluenesulfonyl radical and similar groups. There can be employed especially the protective groups used in the synthesis of peptides and the splitting processes customarily employed in that process. Among others for this purpose reference is made to Jesse P. Greenstein and Milton Winitz "Chemistry of Amino Acids", John Wiley and Sons, Inc., New York (1961) Vol. 2, for example, pages 883 et seq. Also, there can be used carbalkoxy groups (for example of low molecular weight such as carbmethoxy, carbethoxy and carbpropoxy). In the endproduct such acyl groups can be split off by mineral acids such as hydrochloric acid or sulfuric acid, in alcoholic or aqueous-alcoholic solution, or by means of bases, for example, alcoholic alkali lye (for example, methanolic KOH) at temperatures between 20° and 100° C. The benzyl group, the carbobenzoxy radical as well as other reductive splittable radicals can be dehydrogenated with hydrogen in the presence of a hydrogenation catalyst (for example palladium, palladium-carbon) for example in ethanol, for example, under normal conditions.

In compounds which are obtained by process (a) and contain a thiolactone ring, this can be cleaved by known methods. This occurs preferably with basic splitting agents such as NaOH, ammonia or lower aliphatic alcoholates (containing for example 1 to 6, especially 1 to 3 carbon atoms, for example sodium methylate in methanol) at temperatures, for example, between 20° and 60° C.

Furthermore, compounds which are obtained by process (a) and contain a mercapto group can be converted into the corresponding thioethers by customary alkylating agents.

As this type of alkylating agent there can be considered for example, compounds of the formula R'Hal, ArSO$_2$OR' and SO$_2$(OR')$_2$ wherein Hal is a halogen atom (especially chlorine, bromine or iodine) and Ar is an aromatic radical such as phenyl or naphthyl which, for example, in a given case can be substituted by one or more lower alkyl groups and R' is an alkyl group with 1 to 4 carbon atoms. Examples are p-toluene-sulfonic acid alkyl esters having 1 to 4 carbon atoms in the alkyl group, e.g., methyl p-toluenesulfonate, ethyl p-toluenesulfonate, butyl p-toluenesulfonate, methyl phenyl sulfonate, methyl alpha naphthylsulfonate, lower dialkyl sulfates, e.g., dimethyl sulfate, diethyl sulfate and similar esters. For the alkylation reaction the mercaptans are generally added in the form of metal salts, e.g., alkali salts and silver salts, e.g., sodium methyl mercaptide, potassium ethyl mercaptide, sodium butyl mercaptide, silver methyl mercaptide. For example, the reaction occurs at temperatures between 0° and 150° C. in inert solvents such as ethers, e.g., diethyl ether and dioxane, dimethyl formamide, dimethyl sulfoxide, aromatic hydrocarbons, e.g., benzene and toluene.

In process (b) there are added as lactones those lactones which have a 4 to 7 membered lactone ring, for example, beta, gamma or delta lactones. There are especially employed as starting materials such lactone in which the radical —A—COR$_4$ has the structure:

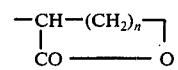

where $n$ is the number 1, 2, 3 or 4. The reaction is carried out in customary solvents or suspension media at higher temperatures such as 100° to 250° C., preferably 150° to 200° C. Suitably there are used sodium or potassium mercaptides of alkyl mercaptans having 1 to 4 carbon atoms.

Esterified carboxyl groups present in the compounds obtained according to processes (a) and (b) can in a given case be saponified by treatment with hydrolyzing agents. For example, there can be used carbalkoxy groups whose alkoxy radicals have 1 to 6 carbon atoms, preferably 1 to 4 carbon atoms, e.g., carbmethoxy, carbethoxy, carbpropoxy, carbobutoxy, carbhexoxy, or the carbobenzoxy group to convert such groups to the free carboxyl group. The saponification can take place for example with bases, (for example methanolic KOH) or in a given case also with mineral acids such as hydrochloric acid or sulfuric acid in alcoholic or aqueous alcoholic solution at temperatures between 20° and 100° C.

In case the structural portion A—COR$_4$ contains a carboxy group the compound of formula I which is obtained can be converted in conventional manner into its metal salts. Thus there can be prepared any pharmacologically acceptable metal salt, especially alkali or alkaline earth metal salts such as sodium, potassium, magnesium and calcium salts. Examples of such salts include the sodium salt of w-(3,4,5-trimethoxybenzoylamino) hexanoic acid, potassium salt of N-(3,4,5-trimethoxybenzoyl) glycine, calcium salt of D,L-N-(3,4,5-trimethoxybenzoyl)valine and magnesium salt of D,L-N-(3,4,5-trimethoxybenzoyl)phenylalanine. The production of the salts can take place by reaction of the free acid with alkali or alkaline earth hydroxides, carbonates, alcoholates or acetates, e.g., sodium hydroxide, potassium hydroxide, calcium hydroxide, magnesium hydroxide, sodium carbonate, potassium carbonate, sodium methylate, potassium ethylate, calcium ethylate, magnesium ethylate, sodium acetate, potassium acetate, magnesium acetate or calcium acetate.

The compounds which contain asymmetrical carbon atoms and as a rule are formed as racemates can be split into the optically active isomers in known manner, for example, by means of an optically active base. However, it is also possible to employ optically active starting materials whereby there is obtained as the end product a corresponding optically active form.

The compounds of the invention are suited for the production of pharmaceutical compositions or preparations. The pharmaceutical compositions or medicines contain one or more of the compounds of the invention as the active material, in a given case in admixture with other pharmacologically or pharmaceutically active materials, of which potassium and magnesium aspartate are preferred. The production of the medicine can be accomplished using known and conventional pharmaceutical carriers and adjuvants.

The medicines can be used for example enterally, parenterally, orally, perlinqually or in the form of sprays. The administration can take place, for example, in the form of tablets, capsules, pills, dragees, plugs, liquids or aerosols. As liquids there can be used for example oily or aqueous solutions or suspensions, emulsions, or injectable aqueous or oily solutions or suspensions.

The activity of the compounds of the invention was investigated on narcotized dogs with acute induced coronary stenosis based on the method of G. V. Anrep and H. Hausler (J. Physiol. Vol. 65 (1928), pages 357-373). For example, it causes an improvement in the bloodflow in the supplying of narrowed coronary vessels.

As general dosage range for the activity, there can be used for example 0.5 to 50 mg/kg intravenously and 1 to 200 mg/kg in oral application.

Starting materials which are not known can be obtained for example as follows:

The production of anhydrides of the formula IV wherein X is the group:

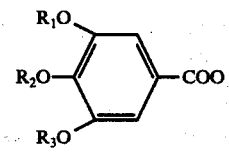 VI can take place by reaction of the corresponding substituted benzoic acid, e.g., 3,4,5-trimethoxybenzoic acid with acetic anhydride in a manner analogous to that specified in HoubenWeyl, "Methoden der organischen Chemie," Vol. 8 (1952) page 447. The production of mixed anhydride of formula IV wherein X is the group —OCOR" for example and R" is an alkoxy or phenoxy group and whose further reaction can also be carried out in a working process by reacting the corresponding substituted benzoic acid, e.g., 3,4,5-trimethoxybenzoic acid with a chloroformic acid alkyl ester (for example a lower alkyl ester such as ethyl chloroformate, methyl chloroformate or butyl chloroformate) or phenyl chloroformate in the presence of a tertiary amine, e.g., triethylamine or tributylamine, and then reacting with the amino carboxylic acid derivative of formula II to form the compound of formula I, according to the procedure described by G. P. Schiemenz and H. Engelhard (Chem. Berichte, Vol. 92 (1959), pages 857-862). (The entire disclosure of Schiemenz et al article is hereby incorporated by reference.) This reaction is preferably carried out in an inert organic medium such as benzene or toluene between −10° and +100° C.

Starting compounds of formula IV wherein X is the group —N≡N can be obtained for example by reacting the corresponding acid hydrazide with nitrous acid according to the directions in Houben-Weyl, Methoden der organischen Chemie, Vol. 8 (1952), page 681.

Starting materials of formula IV wherein X is a group of the formula —O—SO$_3$H, —O—PO(OH)$_2$, —P-(OR')$_2$ or —OAs(OR')$_2$ can be obtained for example from compounds for formula IV wherein X is a halogen atom by reaction with corresponding arsenious acid ester salts, phosphorous acid ester salts or primary sulfates or phosphates, e.g., diethyl sodium arsenite, diethyl sodium phosphite, sodium acid sulfate or monosodium phosphate. Starting materials of formula IV wherein X is the group —OCO—OR" can be obtained for example from alkali metal salts of compounds of formula III by reacting them with compounds of the formula Hal—COOR" (where Hal is chlorine or bromine), e.g., by reacting sodium 3,4,5-trimethoxybenzoate with ethyl chloroformate.

Starting compounds for process (b) can be obtained for example according to the conditions of process (a) by reaction of an aminolactone of formula VI:

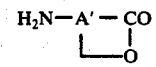

with a benzoyl derivative of the formula IV. In formula VI A' is an unsubstituted straight or branched chain alkylene or alkylidene radical having 2 to 5 carbon atoms.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers and assistants as set forth for example are those recommended in the following literature as adjuvants for pharmacy, cosmetic and related fields such as in Ullmann's Encyklopadie der technischer Chemie, Vol. 4 (1953), pages 1 to 39; Journal of Pharmaceutical Sciences, Vol. 52 (1963), pages 918 et seq.; H. va. Czetsch-Lindenwald, Hilfstoffe fur Pharmazie und angrenzende Gebiete; Pharm. Ind. Vol. 2 (1961), pages 72 et seq.; Dr. H. P. Fiedler, Lexicon der Hilfstoffe fur Pharmazie, Kosmetik und angrenzende Gebiete,, Cantor Kg. Aulendorf i. Wurtt, 1971.

Examples of such materials include gelatin, sugars such as sucrose or lactose, lecithin, pectin, starch (for example corn starch), tylose, talc, lycopodium silica (for example colloidal, glucose, cellulose, cellulose derivatives for example cellulose ethers in which the cellulose hydroxyl groups are partially etherified with lower aliphatic alcohols and/or lower saturated oxyalcohols, for example, methyl hydroxypropyl cellulose, methyl cellulose, hydroxyethyl cellulose), stearates, e.g., methylstearate, and glyceryl stearate, magnesium and calcium salts of fatty acids with 12 to 22 carbon atoms, especially saturated acids (for example calcium stearate and magnesium stearate, emulsifiers, vegetable oils and fats, especially of plant origin (for example, peanut oil, castor oil, olive oil, sesame oil, cottonseed oil, corn oil, mono, di and tri-glycerides of saturated fatty acids ($C_{12}H_{24}O_2$ to $C_{18}H_{36}O_2$ and their mixtures), water, pharmaceutically compatible monoor polyvalent alcohols and polyglycols such as glycerine, mannitol, sorbitol, pentaerythritol, ethyl alochol, diethylene glycol, triethylene glycol, ethylene glycol, propylene glycol dipropylene glycol, polyethylene glycol 400, as well as derivatives of such alcohols and polyglycols, dimethyl sulfoxide, esters of saturated and unsaturated fatty acids (2 to 22 carbon atoms, especially 10 to 18 carbon atoms), with mono- (1 to 20 carbon atoms) alkanols or polyhydric alcohols such as glycols, glycerine, diethylene glycol, pentaerythritol, sorbitol, mannitol, ethyl alcohol, butyl alcohol, octadecyl alcohol, etc., glyceryl stearate, glyceryl palmitate, glyceryl oleate, ethylene glycol stearate; such esters of polyvalent alcohols can in a given case also be etherified, benzyl benzoate, dioxolate, glycerine formal, glycol furfural, dimethyl acetamide, lactamide, lactates, e.g., ethyl lactate, ethyl carbonate, silicones (especially middle viscosity dimethyl polysiloxane) and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol and oleyl alcohol, triglycerides, e.g., glyceryl oleate, glyceryl stearate and glyceryl acetate, partial esters of glycerine, e.g., monoacetic diacetin, glyceryl monostearate, glyceryl distearate, glyceryl monopalmitate, paraffins and the like.

In the production of the preparation there can be used known and conventional solvent aids. As solvent aids there can be used for example polyoxyethylated fats, e.g., polyoxyethylated oleo triglyceride, linolized oleotriglyceride. Examples of oleotriglycerides are olive oil, peanut oil, corn oil (see also Dr. H. P. Fiedler, "Lexikon der Hilfsstoffe fur Pharmazie, Kosmetik und angrenzende Gebiete", 1971, pages 191 to 195.

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Furthermore, there can be added preservatives, stabilizers, buffers, taste correctives, antioxidants and complex formers (for example ethylenediamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used, for example, sodium meta bisulfite, ascorbic acid, gallic acid, alkyl gallates, e.g., methyl gallate and ethyl gallate, butyl hydroxyanisole, nordihydroguararetic acid, tocopherol such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester), benzoic acid, sodium benzoate, trichloroisobutyl alcohol, phenol, cresol, benzethonium chloride and formalin derivatives.

The pharmacological and galenical treatment of the compounds of the invention takes place according to the usual standard methods. For example, the active material or materials and assistants or carriers are well mixed by stirring or homogenization (for example, by means of colloid mill or ball mill), wherein the operation is generally out at temperatures between 20° and 80° C., preferably 20° to 50° C.

The drugs can be used for example orally, parenterally, rectally, vaginally, perlingually, or locally.

Especially, it is possible or preferable to add other medically active materials, above all cardiaca such as heart active steroids, methyl xanthines and/or coronary spasmolytics.

The compounds of the invention on the dog heart in situ show (method according to Anrep and Hausler, J. Physiol. Vol. 65 (1928), pages 357–373) an improvement of ischemic insufficiency induced by artificial stenosisation of the aorta coronaris circumflexa.

This antiischemic activity is comparable to the activity of known medicines which contain nitroglycerine as the active material.

The lowest effective dosage in the above mentioned animal experiments is for example 10 mg/kg body weight orally, 1 mg/kg body weight intravenously.

As a general range of dosage for activity (based on animal studies as above) for example are:

5 to 70 mg/kg body weight orally, 0.1 to 15 mg/kg body weight intravenously.

The compounds of the invention have utility in the prophylaxis and treatment of heart illnesses such as ischemic cardiopathy such as angina pectoris, heart infarct as well as blood flow disturbances in peripheral vessels such as diabetic angiopathy, Morbus Raynard, Claudicatio intermittent, apoplexy consequences, embolism or thrombosis.

The pharmaceutical preparations generally contain between 10 and 300 mg of the active components of the invention.

The compounds can be delivered in the form of tablets, capsules, pills, dragees, suppositories, salves, gels, cremes, powders, liquids, dusts or aerosols. As liquids there can be used oily or aqueous solutions or suspensions, emulsions. The preferred forms of use are tablets which contain between 10 and 50 mg of active material or solutions which contain between 0.5 and 5% of active material.

In individual doses the amount of active component of the invention can be used for example in an amount of:

a. in oral dispensation between 10 and 500 mg,
b. in parenteral dispensation (for example intravenously, intramuscularly) between 10 and 50 mg,
c. in medicines for inhalation (solutions or aerosols) between 0.5 and 2%,
d. in medicines for rectal or vaginal application, between 10 and 50 mg.,
e. in medicines for local application on the skin or mucous membranes (for example in form of solutions, lotions, emulsions, salves, etc.) between 0.5 to 5%.

(The dosages in each case are based on the free base).

For example, there is recommended the use of 1 to 3 tablets containing 50 to 500 mg of active ingredient 3 times daily or for example, intravenously the injection 1 to 3 times daily of a 1 to 5 ml ampoule containing 5 to 50 mg of active substance. In oral preparations the minimum daily dosage for example is 50 mg; the maximum daily dosage should not be over 5 grams.

In the treatment of dogs and cats the oral individual dosage in general is between about 10 and 200 mg/kg body weight; the parenteral dosage is between about 1 to 20 mg/kg body weight.

The acute toxicity of the compounds of the invention in the mouse (expressed by the $LD_{50}$ mg/kg method of Miller and Tainter, Proc. Soc. Exper. Biol. and Med., Vol. 57 (1944) pages 261, et seq.) in oral application is above 2000 mg/kg.

The drugs can be used in human medicine, in veterinary medicine, e.g., to treat cats, dogs, horses, sheep, cattle, goats and pigs or in agriculture. The drugs can be used alone or in admixture with other pharmacologically active materials.

The free acids can also be used as curing agents for melamine-formaldehyde resin.

Unless otherwise indicated all parts and percentages are by weight.

EXAMPLE 1

D,L-N-(3,4,5-trimethoxybenzoyl)methionine:

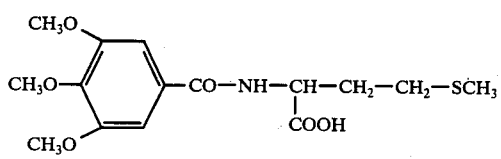

A solution of 14.9 grams (0.1 mole) of D,L-methionine in soda lye (12 grams of NaOH in 200 ml of water) were gradually treated with stirring at room temperature with 25.3 grams (0.11 mole) of 3,4,5-trimethoxybenzoylchloride. Then the mixture was stirred further for 1 hour and acidified with 120 ml of 18% hydrochloric acid while cooling with ice, whereupon the title substance precipitated. It was washed well with ether and subsequently recrystallized from ethanol. Yield 14 grams; M.P. 176° to 177° C.

EXAMPLE 2

D-N-(3,4,5-trimethoxybenzoyl)-methionine

There were gradually added 25.3 grams (0.11 mole) of 3,4,5-trimethoxybenzoyl chloride with stirring at room temperature to a solution of 14.9 grams (0.1 mole) of D-methionine in soda lye (12 grams of NaOH in 200 ml of water) and the mixture subsequently stirred for 1 hour. Then the mixture was acidified with 120 ml of 18% hydrochloric acid, whereupon the title substance precipitated. It was washed well with ether and subsequently recrystallized from 10% ethanol. Yield 17 grams; M.P. 165° to 166° C.

$[\alpha]_D^{20} + 21°$ (in methanol)

EXAMPLE 3

L-N-(3,4,5-trimethoxybenzoyl)-methionine:

There were gradually added 25.3 grams (0.11 mole) of 3,4,5-trimethoxybenzoyl chloride with stirring at room temperature to a solution of 14.9 grams (0.1 mole) of L-methionine in soda lye (12 grams of NaOH in 200 ml of water) and the mixture subsequently stirred for 1 hour. Then the mixture was acidified with 120 ml of 18% hydrochloric acid, whereupon the title substance precipitated. It was washed well with ether and subsequently recrystallized from 10% ethanol. Yield 22 grams; M.P. 165° to 166° C.

$[\alpha]_D^{20} -25°$ (in methanol)

The potassium salt was obtained as follows:

10.3 grams (30 millimoles) of L-N-(3,4,5-trimethoxybenzoyl)-methionine were added with stirring into a solution of 2.2 grams (40 millimoles) of potassium hydroxide in 100 ml of ethanol and further stirred for 2 hours. Then the solvent was distilled off and the residue recrystallized from isopropanol. Yield 11 grams; Decomposition at 105° C.

EXAMPLE 4

D,L-N-(3,4,5-trimethoxybenzoyl)methionine-sulfone:

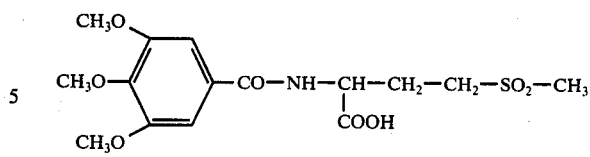

There were gradually added with stirring at room temperature 12.7 grams (55 millimoles) of 3,4,5-trimethoxybenzoyl chloride to a solution of 9 grams (50 millimoles) of D,L-methioninesulfone in soda lye (6 grams of NaOH in 100 ml of water) and the mixture subsequently stirred for 1 hour. Then the mixture was acidified with 60 ml of 18% hydrochloric acid whereupon the title substance precipitated. It was washed well with ether and subsequently recrystallized from ethanol.

Yield 7 grams; M.P. 212° to 213° C.

EXAMPLE 5

D,L-N-(3,4,5-trimethoxy-benzoyl)-ethionine:

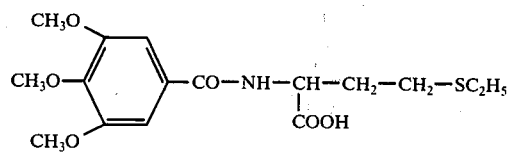

There were gradually added with stirring at room temperature 25.3 grams (0.11 mole) of 3,4,5-trimethoxybenzoyl chloride to a solution of 16.3 grams (0.1 mole) of D,L-ethionine in soda lye (12 grams of NaOH in 200 ml of water) and the mixture subsequently stirred for 1 hour. Then it was acidified with 120 ml of 18% hydrochloric acid, whereupon the title substance precipitated. It was washed well with ether and recrystallized from 20% ethanol.

Yield 23 grams; M.P. 165° to 166° C.

EXAMPLE 6

D,L-N-(3,4,5-trimethoxy-benzoyl)-homocysteinethiolactone:

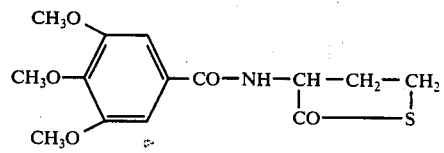

A solution of 15.3 grams (0.1 mole) of D,L-homocysteinethiolactone hydrochlorine in 100 ml of acetone and 16 ml of pyridine were treated with stirring with a solution of 23 grams (0.1 mole) of 3,4,5-trimethoxybenzoyl chloride in 50 ml of acetone and heated one half hour at reflux. After the cooling, the reaction solution was diluted with 300 ml of water and the precipitated product recrystallized from ethanol.

Yield 23 grams; M.P. 173° C.

EXAMPLES OF THE PRODUCTION OF A MEDICINE

EXAMPLE 7

| Composition |  |
|---|---|
| (1) D,L-N-(3,4,5-trimethoxybenzoyl)-methionine (compound of Example 1) | 5.0 mg |

| Composition | |
|---|---|
| (2) Lactose, coarsely powdered | 135.0 mg |
| (3) Avicel (pharmaceutical grade microcrystalline cellulose) | 117.6 mg |
| (4) Magnesium stearate | 2.4 mg |
| | 260.0 mg |

Materials (1), (2), (3) and (4) were sieved (sieve 0.5 mm) and subsequently intensively mixing in a Lodige mixer. Then the mixture was fitted into snap fit-hard gelatin capsules size 2 (0.38 ml).

EXAMPLES OF PHARMACEUTICAL PREPARATIONS

EXAMPLE 8

PRODUCTION OF AN AEROSOL PREPARATION
1 aerosol container contained:

| | |
|---|---|
| D,L-N-(3,4,5-trimethyloxybenzoyl)methionine-sulfone (micronized) (Compound of Example 4) | 400 mg |
| Sorbitan trioleate | 800 mg |
| Monofluorotrichloromethane | 4150 mg |
| Difluorodichloromethane | 5800 mg |
| Tetrafluorodichloroethane | 2850 mg |
| | 14000 mg |

8 grams of sorbitan trioleate were homogeneously mixed with 13 grams of monofluorotrichloromethane in a suitable container. The micronized active material of Example 4 (4 grams) was homogeneously suspended in this mixture. Then with stirring there was added a mixture of 28.5 grams of the tetrafluorodichloroethane, 58 grams of difluorodichloromethane and 28.5 grams of monofluorotrichloromethane cooled to −45° C. (= aerosol suspension). The aerosol suspension was drawn off into aluminum monoblock dosages and sealed with a dosaging valve which set free 0.05 ml of suspension per pressing of the valve.

PRODUCTION OF AN INJECTION SOLUTION

EXAMPLE 9

| | |
|---|---|
| Composition of 2 ml ampoule | |
| Compound of Example 4 | 5 mg |
| Sodium acetate buffer solution, pH = 5.5 | 1 ml |
| Water for injection purposes sufficient to make 2 ml. | |

The active material was dissolved in a mixture of acetate buffer solution and water for injection at 50° to 60° C. with stirring. The solution was filtered, then filled into ampoules and sterilized for 20 minutes at 120° C. The resulting injectable solution was colorless and can be used for intravenous application.

PRODUCTION OF A PLUG PREPARATION

EXAMPLE 10

Production of a Plug Preparation 50 grams of D,L-N-(3,4,5-trimethoxy-benzoyl)-homocysteinethiolactone (Compound) of Example 6) was worked into 1950 grams of molten suppository material (for example hard fat DAB 7) and poured into forms for 2 gram suppositories. 1 suppository contained 50 mg of the Compound of Example 6.

PRODUCTION OF A PREPARATION FOR LOCAL APPLICATION TO THE SKIN

EXAMPLE 11

There were suspended 2 grams of the Compound of Example 6 to a mixture of 6.5 grams of yellow wax, 8 grams of spermaceti, 60 grams of peanut oil and 0.5 gram of glycerine monostearate which had been heated to 60° C.

Then at the same temperature there was worked in 23 grams of preheated water. The mixture stirred until it was cooled off. It contained a yellowish white salve which was soft at room temperature and contained 2% of the active material.

What is claimed is:

1. A pharmaceutical composition having antiischemic activity comprising (1) an effective amount of a compound of the formula;

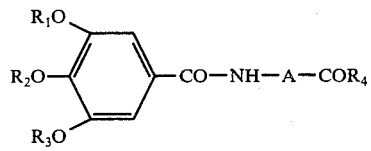

wherein:
A is alkylidene having 2 to 5 carbon atoms and which is substituted by alkyl thio having 1 to 4 carbon atoms, carboxymethyl thio group, carboxyethyl thio, alkylsulfonyl having 1 to 4 carbon atoms, or mercapto, or the substituent on A together with —COR$_4$ forms a 4 to 7 membered thiolactone ring, or A is substituted by an acylmercapto wherein the acyl is benzoyl, benzoyl substituted with one, two or three alkoxy groups with 1 to 6 carbon atoms, alkanoyl of one to six carbon atoms, alkenoyl of 3 to 6 carbon atoms, at least two of R$_1$, and R$_2$ and R$_3$ are alkyl of 1 to 5 carbon atoms and the other R$_1$, R$_2$ and R$_3$ is alkyl of 1 to 5 carbon atoms, hydrogen or the acyl of alkanoic acid of 2 to 4 carbon atoms and R$_4$ is hydroxy or alkoxy with 1 to 5 carbon atoms and their pharmaceutically acceptable salts and (2) a pharmaceutically acceptable adjuvant.

2. A composition according to claim 1 wherein A is propylidene-(1) or butylidene-(1) wherein the propylidene is substituted in the 3 position and the butylidene is substituted in the 4 position with mercapto, alkylthio having 1 to 3 carbon atoms in the alkyl, alkanoylthio having 1 to 3 carbon atoms in the alkanoyl, or alkylsulfonyl having 1 to 3 carbon atoms in the alkanoyl, R$_4$ is hydroxy or alkoxy having 1 to 4 carbon atoms, R$_1$, R$_2$ and R$_3$ are all methyl.

3. A composition according to claim 2 wherein said substituent in the propylidene or butylidene is mercapto, methylthio or methylsulfonyl.

4. A composition according to claim 2 wherein A is said substituted propylidene.

5. A composition according to claim 4 wherein the substituent is alkylthio having 1 to 2 carbon atoms in the alkyl or alkylsulfonyl having 1 to 2 carbon atoms in the alkyl.

6. A composition according to claim 5 wherein the compound is 3,4,5-trimethoxybenzoyl methionine.

7. A composition according to claim 5 wherein the compound is 3,4,5-trimethoxybenzoyl methionine sulfone.

8. A composition according to claim 5 wherein the compound is 3,4,5-trimethoxybenzoyl ethionine.

9. A composition according to claim 1 wherein the compound is 3,4,5-trimethoxybenzoyl homocysteinethiolactone or 3,4,5-trimethoxy benzoyl cysteine thiolactone.

10. A composition according to claim 1 wherein the compound is 3,4,5-trimethoxybenzoyl cysteinethiolactone.

11. A composition according to claim 1 wherein A is 2 to 4 carbon atom alkylene or alkylidene and the substituent on A is alkyl mercapto having 1 to 4 carbon atoms, alkylsulfonyl having 1 to 4 carbon atoms or the substituent on A together with —COR$_4$ forms a homocysteinethiolactone ring or a cysteinethiolactone ring.

12. A composition according to claim 1 wherein the substituent on A is alkylmercapto having 1 to 4 carbon atoms, carboxymethyl thio, carboxyethylthio, mercapto, alkylsulfonyl having 1 to 4 carbon atoms, acylmercapto wherein the acyl is benzoyl, benzoyl substituted with 1, 2 or 3 alkoxy groups having 1 to 4 carbon atoms, alkanoyl of 1 to 4 carbon atoms or the substituent on A together with —COR$_4$ forms

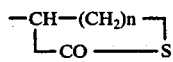

wherein $n$ is 2 or 3 and at least two of R$_1$, R$_2$ and R$_3$ are alkyl of 1 to 4 carbon atoms and the other R$_1$, R$_2$ and R$_3$ is alkyl of 1 to 4 carbon atoms, hydrogen or the acyl of alkanoic acid of 2 to 4 carbon atoms and R$_4$ is hydroxy or alkoxy with 1 to 4 carbon atoms.

13. A composition according to claim 1 wherein A is substituted by alkyl sulfonyl having 1 to 4 carbon atoms.

14. A composition according to claim 1 wherein A is substituted by carboxymethylthio or carboxyethylthio.

15. A composition according to claim 1 wherein A together with —COR$_4$ forms

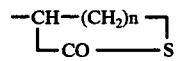

where $n$ is 2 or 3.

16. A composition according to claim 1 wherein A is alkylidene having 2 to 5 carbon atoms and which is substituted by alkyl thio having 1 to 4 carbon atoms or mercapto, at least two of R$_1$, R$_2$ and R$_3$ are alkyl of 1 to 5 carbon atoms and the other R$_1$, R$_2$ and R$_3$ is alkyl of 1 to 5 atoms, hydrogen or the acyl of alkanoic acid of 2 to 4 carbon atoms and R$_4$ is hydroxy or alkoxy with 1 to 5 carbon atoms.

17. A composition according to claim 16 which is a tablet containing 50 to 500 mg of said compound.

18. A composition according to claim 1 containing 10 to 500 mg of said compound.

19. A composition according to claim 1 which is a solution containing 0.5 to 5% of said compound.

20. A composition according to claim 1 which is an aerosol containing 0.5 to 2% of said compound.

21. A method of treating an ischemic circulatory heart illness in a mammal comprising administering to the mammal an antiischemic effective dosage to treat said illness of a compound of the formula:

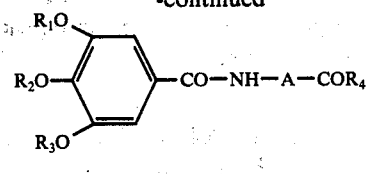

wherein:

A is alkylidene having 2 to 5 carbon atoms and which is substituted by alkyl thio having 1 to 4 carbon atoms, carboxymethyl thio, carboxyethyl thio, an alkylsulfonyl having 1 to 4 carbon atoms, or mercapto, or the substituent on A together with —COR$_4$ forms as 4 to 7 membered thiolactone ring, or A is substituted by acylmercapto wherein the acyl is benzoyl, benzoyl substituted with one, two or three alkoxy groups with 1 to 6 carbon atoms, an alkanoyl of one to six carbon atoms, alkenoyl of 3 to 6 carbon atoms, at least two of R$_1$, R$_2$ and R$_3$ are alkyl of 1 to 5 carbon atoms and the other R$_1$, R$_2$ and R$_3$ is alkyl of 1 to 5 carbon atoms, hydrogen or the acyl of alkanoic acid of 2 to 4 carbon atoms and R$_4$ is hydroxy or alkoxy with 1 to 5 carbon atoms and their pharmaceutically acceptable salts.

22. A method according to claim 21 wherein A is propylidene-(1) or butylidene-(1) wherein the propylidene is substituted in the 3 position and the butylidene is substituted in the 4 position with mercapto, alkylthio having 1 to 3 carbon atoms in the alkyl, alkanoylthio having 1 to 3 carbon atoms in the alkanoyl, or alkylsulfonyl having 1 to 3 carbon atoms in the alkanoyl, R$_4$ is hydroxy or alkoxy having 1 to 4 carbon atoms, R$_1$, R$_2$ and R$_3$ are all methyl.

23. A method according to claim 22 wherein said substituent in the propylidene or butylidene is mercapto, methylthio or methylsulfonyl.

24. A method according to claim 22 wherein A is said substituted propylidene.

25. A method according to claim 24 wherein the substituent is alkylthio having 1 to 2 carbon atoms in the alkyl or alkylsufonyl having 1 to 2 carbon atoms in the alkyl.

26. A method according to claim 25 wherein the compound employed is 3,4,5-trimethoxybenzoyl methionine.

27. A method according to claim 25 wherein the compound is 3,4,5-trimethoxybenzoyl methionine sulfone.

28. A method according to claim 25 wherein the compound is 3,4,5-trimethoxybenzoyl ethionine.

29. A method according to claim 21 wherein the compound is 3,4,5-trimethoxybenzoyl homocysteinethiolactone or 3,4,5-trimethoxybenzoyl cysteine thiolactone.

30. A method according to claim 21 wherein the compound is 3,4,5-trimethoxybenzoyl cysteinethiolactone.

31. A method according to claim 21 wherein A is 2 to 4 carbon atom alkylene or alkylidene and the substituent on A is alkyl mercapto having 1 to 4 carbon atoms, alkylsulfonyl having 1 to 4 carbon atoms or the substituent on A together with —COR$_4$ forms a homocysteinethiolactone ring or a cysteinethiolactone ring.

32. A method according to claim 21 wherein the substituent on A is alkylmercapto having 1 to 4 carbon atoms, carboxymethyl thio, carboxyethylthio, mercapto, alkylsulfonyl having 1 to 4 carbon atoms, acylmercapto wherein the acyl is benzoyl, benzoyl substituted with 1, 2 or 3 alkoxy groups having 1 to 4 carbon atoms, alkanoyl of 1 to 4 carbon atoms or the substituent on A together with —COR$_4$ forms

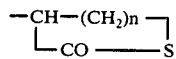

wherein $n$ is 2 or 3 and at least two of R$_1$, R$_2$ and R$_3$ are alkyl of 1 to 4 carbon atoms and the other R$_1$, R$_2$ and R$_3$ is alkyl of 1 to 4 carbon atoms, hydrogen or the acyl of alkanoic acid of 2 to 4 carbon atoms and R$_4$ is hydroxy or alkoxy with 1 to 4 carbon atoms.

33. A method according to claim 21 wherein A is substituted by alkylsulfonyl having 1 to 4 carbon atoms.

34. A method according to claim 21 wherein A is substituted by carboxymethylthio or carboxyethylthio.

35. A method according to claim 21 wherein A together with —COR$_4$ forms

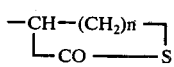

where $n$ is 2 or 3.

36. A method according to claim 21 wherein the dosage is applied orally and is 5 to 70 mg/kg body weight.

37. A method according to claim 21 wherein the dosage is applied orally and is 10 to 500 mg.

38. A method according to claim 21 wherein the dosage is applied orally and is 50 to 300 mg.

39. A method according to claim 21 wherein the dosage is applied intrevenously and is 0.1 to 15 mg/kg body weight.

40. A method according to claim 21 wherein the dosage is applied intravenously and is 10 to 50 mg.

41. A method according to claim 21 wherein the dosage is applied intravenously and is 0.1 to 15 mg/kg body weight.

42. A method according to claim 21 wherein the dosage is applied rectally and is 10 to 50 mg.

43. A method according to claim 21 wherein the dosage is applied vaginally and is 10 to 50 mg.

44. A method according to claim 21 wherein the dosage is applied by inhalation as an 0.5 to 2% solution or aerosol.

45. A method according to claim 21 wherein the dosage is applied by local application topically at a concentration of 0.5 to 5%.

46. A method according to claim 21 wherein A is alkylidene having 2 to 5 carbon atoms and which is substituted by alkyl thio having 1 to 4 carbon atoms or mercapto, at least two of R$_1$, R$_2$ and R$_3$ are alkyl of 1 to 5 carbon atoms and the other R$_1$, R$_2$ and R$_3$ is alkyl of 1 to 5 atoms, hydrogen or the acyl of alkanoic acid of 2 to 4 carbon atoms and R$_4$ is hydroxy or alkoxy with 1 to 5 carbon atoms.

* * * * *